(12) United States Patent
Diehl et al.

(10) Patent No.: US 6,392,044 B1
(45) Date of Patent: May 21, 2002

(54) RACEMIZATION OF R,S-DIOXO-BENZYLPYRROLOPIPERIDINE

(75) Inventors: Herbert Diehl, Leverkusen; Georg Martin, Langenfeld; Wilfried Jaworek, Köln; Andreas Krebs, Odenthal; Joachim Westen, Solingen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/608,471

(22) Filed: Jun. 30, 2000

(30) Foreign Application Priority Data

Jul. 6, 1999 (DE) .......................... 199 31 115

(51) Int. Cl.⁷ .................. C07D 471/04; C07D 487/04
(52) U.S. Cl. .................. 546/113; 546/112; 540/505
(58) Field of Search ................. 546/112, 113; 540/505

(56) References Cited

U.S. PATENT DOCUMENTS

| | | | |
|---|---|---|---|
| 4,051,140 A | 9/1977 | Gelbein et al. | 260/290 P |
| 4,401,819 A | 8/1983 | Cordier et al. | 546/252 |
| 4,990,517 A | 2/1991 | Petersen et al. | 514/300 |
| 5,059,597 A | 10/1991 | Petersen et al. | 514/224.5 |
| 5,416,096 A | 5/1995 | Petersen et al. | 514/312 |
| 5,607,942 A | 3/1997 | Petersen et al. | 546/200 |

FOREIGN PATENT DOCUMENTS

| | | |
|---|---|---|
| CA | 2086914 | 11/1993 |
| CA | 2108060 | 4/1994 |
| DE | 199 27 412 | 12/2000 |
| GB | 1157001 | 7/1969 |
| GB | 1569486 | 7/1980 |

OTHER PUBLICATIONS

Elco j. Ebbers et al, Tetrahedron report No. 423 pp. 9417–9476, 1997.*

Tetrahedron, vol. 53, No. 28, (month unavailable) 1997, pp. 9417–9476, Ebbers et al.

Controlled Racemization of Optically Active Organic Compounds: Prospects for Asymmetric Transformation.

* cited by examiner

*Primary Examiner*—Alan L. Rotman
*Assistant Examiner*—Rita Desai
(74) *Attorney, Agent, or Firm*—Joseph C. Gil; Diderico van Eyl

(57) ABSTRACT

Cis-R-dioxo-benzylpyrrolopiperidine is racemized in a particularly advantageous manner by treating it with a substoichiometric amount of base, preferably at temperatures below about 40° C.

10 Claims, No Drawings

RACEMIZATION OF R,S-DIOXO-BENZYLPYRROLOPIPERIDINE

BACKGROUND OF THE INVENTION

The present invention relates to a process for racemizing (1R,6S)-8-benzyl-7,9-dioxo-2,8-diazabicyclo[4.3.0]nonane, also referred to here as R-DOPP or R,S-dioxobenzylpyrrolopiperidine, by reaction with a base.

For preparing the quinolone derivative described in EP-A 350 733, enantiomerically pure (S,S)-2,8-diazabicyclo [4.3.0]nonane, hereinbelow also referred to as cis-S,S-pyrrolopiperidine, is required, and this compound can be obtained from enantiomerically pure (1S,6S)-8-benzyl-2,8-diazabicyclo[4.3.0]nonane, hereinbelow also referred to as S-BEPP or S-benzylpyrrolopiperidine, by debenzylation. It is known that S-BEPP can be obtained from racemic cis-benzylpyrrolopiperidine via racemate resolution using tartaric acid (EP-A 550 903). The resulting undesired enantiomer (R,R)-8-benzyl-2,8-diazabicyclo[4.3.0]nonane, hereinbelow also referred to as R-BEPP, cannot be used any further. This process has the disadvantages that the undesired enantiomer, which is useful per se, is lost and that its disposal involves costs.

According to the applicant's earlier proposal (DE-A 199 27 412), the racemate resolution can be carried out at an earlier stage of the synthesis of cis-S,S-pyrrolopiperidine. Here, the enantiomers are, at the stage of racemic DOPP, hereinbelow also referred to as rac-DOPP, separated by racemate resolution using (–)-2,3:4,6-di-O-isopropylidene-2-oxo-L-gulonic acid, as its salts. Liberation from the corresponding salts gives S-DOPP (which is (1S,6R)-8-benzyl-7,9-dioxo-2,8-diazabicyclo[4.3.0]nonane) and R-DOPP.

A number of routes for racemizing R-DOPP and possible recycling of the undesired enantiomer are conceivable. On the one hand, the two stereocenters can be eliminated by dehydrogenating the undesired enantiomer to give a mixture of the pyridine or tetrahydropyridine derivative, and the dehydrogenation mixture can then be rehydrogenated to give the racemate. It is already known that pyridines can be prepared from the corresponding piperidines.

Thus, GB Patent Specification 1 157 001 describes a process for preparing pyridines by reacting the corresponding piperidines with oxygen and ions of copper, iron or cobalt in liquid phase at from about 120 to about 150° C., using acetic acid as solvent.

According to EP-A 61 982, pyridines and substituted pyridines are obtained by reacting the corresponding piperidines in the gas phase at temperatures of from about 200 to about 500° C. on a Pd or Pt contact, possible substituents being alkyl and 1,5-diaminopentane groups.

U.S. Pat. No. 4,051,140 describes the dehydrogenation of piperidines in the presence of oxygen in the gas phase at a vanadium contact at from about 260 to about 540° C. Here, too, mainly alkyl-substituted piperidines are employed.

The gas-phase dehydrogenations described require high reaction temperatures, so that this reaction can only be used for compounds which are stable at these temperatures, which does not apply to R-DOPP. Owing to oxygen being used, the liquid process described requires increased safety precautions.

Before it is possible to recycle the racemate into the preparation process for the quinolone derivative, all dehydrogenations require the hydrogenation of the resulting compound as an additional reaction step.

Overall, racemization by dehydrogenation is either unsuitable in principle for industrial application in the present case, or, owing to the particular safety precautions and additional reaction steps, it is technically complex and inefficient.

On the other hand, it is possible to consider racemization as basic isomerization. Basic racemization would take place by abstraction of a proton from a chiral center and formation of a carbanion. The carbanion would have to be stabilized by one or more neighbouring keto, ester, nitrile and/or nitro groups. Subsequent protonation would then usually afford the racemate. Such racemizations are known in particular for amino acids and amino acid derivatives having <u>one</u> chiral center (see Tetrahedron 53, 9417 (1997)).

However, in the case of R-DOPP, the reaction would have to involve <u>two</u> chiral centers, since in the case of only partial racemization it may be that the corresponding trans compound is formed. Thus, basic racemization cannot be readily applied to the racemization of R-DOPP.

SUMMARY OF THE INVENTION

We have now found a process for racemizing R-DOPP which is characterized in that R-DOPP is treated with a substoichiometric amount of base. These and other features, aspects, and advantages of the present invention will become better understood with reference to the following description and appended claims.

DETAILED DESCRIPTION OF THE INVENTION

For the racemization according to the invention, it is possible to use pure R-DOPP or mixtures comprising predominantly R-DOPP, for example mixtures comprising more than 75% by weight, preferably more than 80% by weight, of R-DOPP. The remainder to 100% by weight of these mixtures can be S-DOPP.

Suitable bases for the racemization according to the invention are, for example, alkoxides, and these can correspond to the formula (I)

$$MOR \qquad (I),$$

in which

M represents lithium, sodium or potassium and

R represents a straight-chain or a branched $C_1$–$C_6$-alkyl group.

In the formula (I), M preferably represents sodium or potassium and R preferably represents methyl or tert-butyl. Preferred individual compounds of the formula (I) include sodium methoxide, sodium tert-butoxide and potassium tert-butoxide. Particular preference is given to potassium tert-butoxide.

The alkoxides can be added in solid form or dissolved in a solvent. Suitable solvents include solvents such as alcohols and aprotic solvents. Examples of suitable alcohols include the alcohol which corresponds to the respective alkoxide used and straight-chain, branched and cyclic ethers, and also aromatic hydrocarbons. Specific examples of aprotic solvents are: methyl tert-butyl ether, tetrahydrofuran, dioxane, toluene and xylene. Preferred alkoxide solutions are: potassium tert-butoxide in tert-butanol and in tetrahydrofuran and sodium methoxide in methanol.

The use of alkoxides in solid form or of a small amount of a concentrated alkoxide solution may result in the formation of reaction mixtures which cannot be stirred or are poorly stirrable. In such cases, it is necessary to make the reaction mixture readily stirrable by adding one or more solvents, for example alcohols and/or ethers of the type described above.

For carrying out the racemization according to the invention, it is not necessary for the R-DOPP used and the base used to be present completely dissolved. However, the amount of alcohol and/or aprotic solvent present should be such that a reaction mixture is obtained which is readily stirrable.

Depending on the choice of solvent, it is possible to carry out the racemization in relatively highly concentrated reaction mixtures. Thus, if the solvent used is, for example, tetrahydrofuran, the concentration of R-DOPP in the solvent can be up to about 50% by weight.

The base can be used, for example, in an amount from about 1 to about 20 mol %, based on the R-DOPP used. This amount is preferably from about 2 to about 15 mol %, in particular from about 3 to about 10 mol %.

To minimize undesirable side reactions, it is advantageous to carry out the racemization according to the invention under substantial exclusion of oxygen. To this end, it is possible, for example, to flush the reaction vessel with an inert gas prior to charging the reactants, and to carry out the racemization under an atmosphere of inert gas. Suitable inert gases are, for example, nitrogen and noble gases, such as argon.

The racemization according to the invention can be carried out, for example, at temperatures below about 40° C. For low temperatures, care has to be taken not to choose a temperature where the reaction mixture is no longer readily stirrable. At which temperature the stirrability is no longer sufficient depends essentially on the type and the amount of solvents present. If appropriate, the temperature at which a given reaction mixture is no longer readily stirrable can be determined by simple routine preliminary experiments. The racemization is preferably carried out at temperatures in the range from about −10 to about +30° C.

The racemization according to the invention has generally ended after at most 5 hours. Under suitable reaction conditions (for example appropriate selection of the base, the solvent and the temperature), the reaction time required can be significantly shorter, for example only 15 minutes or even less.

The reaction mixture that is present after the racemization can be worked up by initially neutralizing the base employed, e.g., by addition of an organic acid such as a $C_1$–$C_6$-carboxylic acid, a mineral acid, e.g., sulfuric acid or phosphoric acid, carbonic acid or an acidic ion exchanger. The amount of acid or acidic ion exchanger used can range from amounts such as from about 0.9 to about 1.1 equivalents per equivalent of base used. This amount is preferably from about 0.97 to about 1.03 equivalents per equivalent of base employed, and the acid or the acidic ion exchanger are in particular employed in equivalent amounts, based on the base used. The solvent can then be removed by any suitable method, e.g., by stripping, if appropriate, under reduced pressure. What then remains is a mixture comprising essentially rac-DOPP and the salt obtained in the neutralization. This mixture can, for example, be processed further in two different ways, by a) taking it up at elevated temperature in a suitable solvent, e.g., an alcohol or an aromatic hydrocarbon, cooling the clear solution, precipitating the resulting rac-DOPP, if appropriate after seeding with solid rac-DOPP, filtering off the rac-DOPP and then washing and drying it, or b) dissolving it in a suitable solvent, e.g, a ketone, filtering off the residual salt and using for further downstream processes the thus obtained solution, for example the thus obtained ketonic solution of the rac-DOPP.

Preferred solvents for route a) include isopropanol and toluene. A preferred solvent for route b) is methyl ethyl ketone.

The racemization according to the invention has the advantage that it goes to completion, that the feared formation of trans compounds is virtually not observed, and that it can be carried out very effectively in a technically simple manner. The racemate can be recycled into the preparation process for the quinolone derivative, making the preparation of this quinolone derivative considerably more efficient, since the undesired isomer, which is useful per se, can be re-used. Moreover, the procedure according to the invention requires only simple chemicals and no particular precautions.

The invention is further described in the following illustrative examples in which all parts and percentages are by weight unless otherwise indicated.

EXAMPLES

Example 1

Under nitrogen, 292 g of tetrahydrofuran were initially charged in a 1000 ml 4-necked-flask, and 300 g of a mixture including 91.4% by weight of R-DOPP and 8.6% by weight of S-DOPP were introduced. The mixture was stirred until a clear yellow solution had been obtained. At room temperature, 11.65 g of a 32% by weight strength solution of potassium tert-butoxide (2.8 mol %, based on the sum of R-DOPP and S-DOPP) in tetrahydrofuran were then added. This gave an orange solution which was stirred at room temperature for 1 hour. 4.15 g of acetic acid were then added, resulting in a change of the color of the solution from orange to yellow and precipitation of potassium acetate. Using a rotary evaporator, the resulting suspension was freed of tetrahydrofuran and then taken up in 183 g of isopropanol. The solution, which was clear at 40° C., was cooled to 28° C. and seeded with rac-DOPP. The rac-DOPP present in the solution then began to precipitate out, resulting in the formation of a suspension which was difficult to stir. The suspension was cooled to 0° C. and the precipitate was filtered off with suction. The filter cake was washed with 60 g of isopropanol at 0° C. and dried under reduced pressure. This gave 225.5 g (87.8% of theory) of rac-DOPP in which the ratio of R-DOPP to S-DOPP was 49.9:50.1.

Example 2

Under nitrogen, 262 g of toluene were initially charged in a 500 ml 4-necked-flask, and 50 g of a mixture including 96% by weight of R-DOPP and 4% by weight of S-DOPP were introduced. The mixture was stirred until a clear yellow solution had been obtained. At room temperature, 3.56 g of a 30% by weight strength solution of sodium methoxide in methanol were then added (this corresponds to 9.9 mol % of sodium methoxide, based on the sum of R-DOPP and S-DOPP). This gave an orange solution which was stirred at room temperature for 1 hour and then admixed with 1.18 g of acetic acid, resulting in the color of the solution changing to yellow. The precipitated sodium acetate was filtered off. Using a rotary evaporator, the filtrate was freed of toluene. This gave 47.1 g of an oily product which crystallized at room temperature. The product was rac-DOPP comprising R-DOPP and S-DOPP in a ratio of 44:55. The yield corresponded to 84.5% of theory.

Example 3

Under nitrogen, 50 g of tetrahydrofuran were initially charged in a 250 ml 4-necked-flask, and 50 g of a mixture comprising S-DOPP and R-DOPP in a ratio of 5.4:94.6 were introduced. The mixture was stirred until a clear yellow solution had been obtained. At room temperature, 1.03 g of potassium tert-butoxide were then added (4.8 mol %, based on the sum of S-DOPP and R-DOPP). This gave an orange solution which was stirred for 4 hours and then admixed with 1.18 g of acetic acid. The color of the solution changed to yellow. Using a rotary evaporator, the reaction mixture was freed of tetrahydrofuran and taken up in methyl ethyl ketone. This gave 113 g of a 32.8% by weight strength solution, which corresponded to a yield of 80% of theory. The ratio of R-DOPP to S-DOPP was 50.6:49.4.

Example 4

Under nitrogen, 150 ml of toluene were charged in a 250 ml 4-necked-flask, and 24.0 g of a mixture comprising S-DOPP and R-DOPP in an enantiomer ratio of 0.2:99.8 were introduced. The mixture was stirred until a clear yellow solution had been obtained, and 4.3 g of solid sodium methoxide were then added at room temperature (24.5 mol %, based on R-DOPP). This gave an orange solution which was stirred at room temperature for 2 hours and then admixed with 1.4 g of acetic acid. This resulted in the color changing to yellow. Using a rotary evaporator, the reaction mixture was freed of toluene. This gave 21.5 g of rac-DOPP (yield 86.5% of theory). The enantiomer ratio of R-DOPP to S-DOPP was 49.8:50.2.

Example 5

Over a period of 1 hour, a) 244.3 g of a 20% by weight strength methanolic solution of a mixture comprising S-DOPP and R-DOPP in an enantiomer ratio of 8:92 and b) 36 g of a 30% by weight strength solution of sodium methoxide in methanol were simultaneously added dropwise to a reaction tube filled with glass rings. After a residence time of 1 hour, the reaction solution was neutralized by metered addition of acetic acid. The resulting ratio of S-DOPP to R-DOPP in the reaction mixture was 57.7:42.5.

Example 6

In a passivated stirred vessel, 476.4 g of a 50.3% by weight strength solution of R-DOPP in tetrahydrofuran were initially charged. The clear yellow solution was cooled to −5° C. 27.5 g of a 20% by weight strength solution of potassium tert-butoxide in tetrahydrofuran were then added. The color of the solution changed to red. The solution was stirred for 30 minutes. 3.0 g of acetic acid were then added, resulting in the color changing back to yellow and the mixture becoming turbid owing to precipitating potassium acetate. This gave 504.5 g of a 44.6% by weight strength solution of rac-DOPP in tetrahydrofuran. The yield was 93.9% of theory. The enantiomer ratio of R-DOPP to S-DOPP was 48.9:51.1.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for racemizing (1R,6S)-8-benzyl-7,9-dioxo-2,8-diazabicyclo[4.3.0]nonane comprising treating the (1R,6S)-8-benzyl-7,9-dioxo-2,8-diazabicyclo[4.3.0]nonane with a substoichiometric amount of base.

2. Process according to claim 1, wherein the (1R,6S)-8-benzyl-7,9-dioxo-2,8-diazabicyclo[4.3.0]nonane is employed in the form of a mixture comprising more than 75% by weight of the(1R,6S)-8-benzyl-7,9-dioxo-2,8-diazabicyclo[4.3.0]nonane.

3. Process according to claim 1, wherein the base used is an alkoxide of the formula (I)

MOR   (I)

in which

M represents lithium, sodium or potassium, and

R represents a straight-chain or a branched $C_1$–$C_6$-alkyl group.

4. Process according to claim 3, wherein the alkoxide is added in solid form.

5. Process according to claim 3, wherein the alkoxide is added dissolved in a solvent.

6. Process according to claim 5, wherein the amount of solvent present is such that a readily stirrable reaction mixture is obtained.

7. Process according to claim 1, wherein the base is employed in an amount ranging from about 1 to about 20 mol %, based on the (1R,6S)-8-benzyl-7,9-dioxo-2,8-diazabicyclo[4.3.0]nonane used.

8. Process according to claim 1, wherein the process is carried out with a substantial exclusion of oxygen and at a temperature below about 40° C.

9. Process according to claim 5, wherein the process further comprises (a) working up the reaction mixture which is present after racemization by neutralizing the base employed, (b) removing the solvent and taking up the remaining mixture in an alcohol or an aromatic hydrocarbon at an elevated temperature and forming a clear solution, (c) cooling the clear solution, (d) precipitating the resulting racemic 8-benzyl-7,9-dioxo-2,8-diazabicyclo[4.3.0]nonane, (e) filtering off the 8-benzyl-7,9-dioxo-2,8-diazabicyclo[4.3.0]nonane; and (f) washing and drying the 8-benzyl-7,9-dioxo-2,8-diazabicyclo[4.3.0]nonane.

10. Process for racemizing (1R,6S)-8-benzyl-7,9-dioxo-2,8-diazabicyclo[4.3.0]nonane comprising (a) treating the (1R,6S)-8-benzyl-7,9-dioxo-2,8-diazabicyclo[4.3.0]nonane with a substoichiometric amount of base comprising an alkoxide of the formula (I)

MOR   (I)

in which

M represents lithium, sodium or potassium, and

R represents a straight-chain or a branched $C_1$–$C_6$-alkyl group (b) working up the reaction mixture which is present after racemization by neutralizing the base, (c) removing the solvent and taking up the remaining mixture in an alcohol or an aromatic hydrocarbon at an elevated temperature, (d) dissolving the mixture which remains after removal of the solvent in a ketone, and (e) filtering off the salt that remains, wherein the resultant racemic 8-benzyl-7,9-dioxo-2,8-diazabicyclo[4.3.0]nonane which has been prepared is used for further downstream processes in form of the thus obtained ketonic solution.

* * * * *